United States Patent [19]
Schwan

[11] 3,966,740
[45] June 29, 1976

[54] 2-METHYL-3-PHENYL-1,2,3,7,8,8a-HEXAHYDRO-1H-CYCLOPENT[i,j]-ISOQUINOLINE HYDROBROMIDE

[75] Inventor: Thomas J. Schwan, Norwich, N.Y.

[73] Assignee: Morton-Norwich Products, Inc., Norwich, N.Y.

[22] Filed: Mar. 7, 1975

[21] Appl. No.: 556,467

[52] U.S. Cl. .................. 260/286 R; 260/283 R; 260/570.6; 424/258
[51] Int. Cl.² ........................................ C07D 217/14
[58] Field of Search ........................ 260/286 R

[56] References Cited
UNITED STATES PATENTS
3,247,210  4/1966  Carson ........................ 260/286

OTHER PUBLICATIONS
Schwan, J. Heterocycl. Chem. (1971), vol. 8 (5), p. 839.

Primary Examiner—Paul M. Coughlan, Jr.
Attorney, Agent, or Firm—Anthony J. Franze

[57] ABSTRACT

A compound 2-methyl-3-phenyl-1,2,3,7,8,8a-hexahydro-1H-cyclopent[i,j]-isoquinoline hydrobromide of the formula:

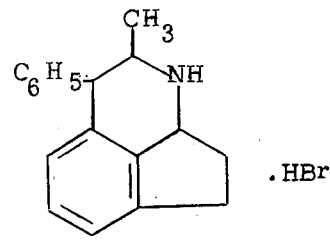

possesses pharmacological activity as an antidepressant.

1 Claim, No Drawings

2-METHYL-3-PHENYL-1,2,3,7,8,8A-HEXAHYDRO-1H-CYCLOPENT[I,J]-ISOQUINOLINE HYDROBROMIDE

This invention relates to a chemical compound. In particular it is concerned with a compound of the formula:

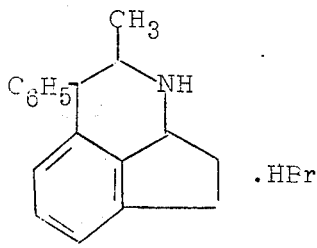

This compound possesses pharmacological activity affecting the central nervous system. When administered perorally to animals it exhibits antidepressant action. Its antidepressant property is evidienced in the control of tetrabenazine-induced ptosis in mice. An oral dose of 50 mg/kg of this compound mice intraperitoneally receiving 35 mg/kg of tetrabenazine counteracts the ptosis producing property of tetrabenazine.

In order that this invention be readily available to and understood by those skilled in the art the following illustration is included:

A. 2-(1-Indanylamino)-1-phenylpropanol hydrochloride

A mixture of 50 g (0.378 mole) of 1-indanone, 57.0 g (0.378 mole) of 2-amino-1-phenylpropanol, 2.0 g p-toluenesulfonic acid monohydrate and 250 ml. toluene was stirred and refluxed using a Dean-Stark apparatus until the theoretical amount of water was collected. The solvents were removed in vacuo and the residue was dissolved in 750 ml. CH$_3$OH. The solution was stirred at 15°–20° while sodium borohydride (15.2 g, 0.40 mole) was added over 10 minutes. The mixture was stirred at 10°–20° for 3.0 hours, diluted with 750 ml. H$_2$O and extracted with 2 × 300 ml. chloroform. The combined chloroform extracts were dried (MgSO$_4$) and concentrated to dryness in vacuo. Treatment of an ethanolic solution of the residue with ethanolic hydrogen chloride gave in two crops 62.0 g (54%) of the product.

B. 2-Methyl-3-phenyl-1,2,3,7,8,8a-hexahydro-1H-cyclopent[i,j]isoquinoline hydrobromide A mixture of 31.6g(0.104 mole) of A and 400 ml 48HBr was stirred and refluxed for 6.0 hours. The mixture was cooled and stirred in an ice bath for 30 minutes and the solid was filtered through a medium sintered glass funnel. The solid was air dried and then recrystallized from 600 ml. CH$_3$CN to give 13.40 g (40%) of the product, m.p. 190°–200°. Further recrystallization from acetonitrile gave the analytical sample, m.p. 207°–210°.

Anal. Calcd. for C$_{18}$H$_{19}$N.HBr: C, 65.46; H, 6.10; N, 4.24. Found: C, 65.19; H, 6.28; N, 4.18.

What is claimed is:
1. A compound of the formula:

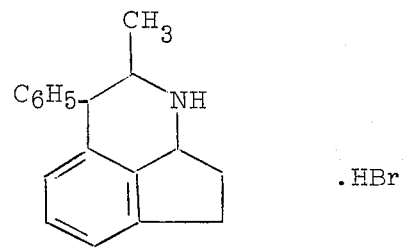

* * * * *